US00PP17179P2

(12) United States Plant Patent
White

(10) Patent No.: US PP17,179 P2
(45) Date of Patent: Oct. 31, 2006

(54) ***EPIMEDIUM* PLANT NAMED 'FIRE DRAGON'**

(50) Latin Name: *Epimedium davidii×leptorrhizum*
Varietal Denomination: FIRE DRAGON

(76) Inventor: Anthony Robin White, Blackthorn Nursery Kilmeston Alresford, Hampshire S024 0NL (GB)

( * ) Notice: Subject to any disclaimer, the term of this patent is extended or adjusted under 35 U.S.C. 154(b) by 0 days.

(21) Appl. No.: 11/190,345

(22) Filed: Jul. 26, 2005

(51) Int. Cl.
*A01H 5/00* (2006.01)

(52) U.S. Cl. ..... Plt./263

(58) Field of Classification Search ..... Plt./263
See application file for complete search history.

(56) References Cited

PUBLICATIONS

Harris et al. Plant Identification Terminology an Illustrated Glossary 2nd ed. 2001, p. 23.*

* cited by examiner

*Primary Examiner*—Kent Bell
*Assistant Examiner*—June Hwu

(57) ABSTRACT

A new cultivar of *Epimedium* plant named 'FIRE DRAGON' that is charaterized by clumping habit, yellow-green and grey-brown leaflets, with large red and yellow, spurred flowers that are held above two distinct layers of foliage. In combination these traits set 'FIRE DRAGON' apart from all other existing varieties of *Epimedium* known to the inventor.

3 Drawing Sheets

Genus: *Epimedium*. Species: *davidii×leptorrhizum*. Denomination: 'FIRE DRAGON'.

BACKGROUND OF THE INVENTION

The present invention relates to a new and distinct cultivar of bishop's hat grown for use as an ornamental for container, rock garden, or as a groundcover for the landscape. The new cultivar is known botanically as *Epimedium davidii×E. leptorrhizum* and will be referred to hereinafter by the cultivar name 'FIRE DRAGON'.

'FIRE DRAGON' is a plant hybrid that resulted from the deliberate cross-hybridization of *Epimedium davidii* (unpatented) and *Epimedium leptorrhizum* (unpatented). The seed parent is an individual *Epimedium davidii* and the pollen parent is an individual *Epimedium leptorrhizum*. The deliberate cross hybridization was conducted in 1992 by the inventor at the inventor's nursery in Hampshire, England.

The new *Epimedium* variety named 'FIRE DRAGON' is readily distinguishable from the seed parent and the pollen parent, by flower size and flower color. The inventor selected 'FIRE DRAGON' in 1992 based on the distinguishing characteristics of flower size and flower color. There are no close comparison plants known to the inventor.

'FIRE DRAGON' is semi-evergreen, characterized by clumping habit, yellow-green and grey-brown leaflets, with large red and yellow, spurred flowers that are held above the leaves. Two distinct layers of foliage are exhibited due to the difference in length between basal stems and the subsequently basally branching stems. Essentially herbaceous, 'FIRE DRAGON' will retain leaves when winter temperatures are above minus 10° Centigrade.

The first asexual reproduction of the new *Epimedium* cultivar 'FIRE DRAGON' was conducted in 1993 by the method of division. Division of 'FIRE DRAGON' was accomplished by the inventor at the inventor's nursery in Hampshire, England. Since that time the distinguishing characteristics of 'FIRE DRAGON' have been determined stable, fixed and reproduce true to type in successive generations.

SUMMARY OF THE INVENTION

The following traits have been repeatedly observed and represent the characteristics of the new *Epimedium* cultivar named 'FIRE DRAGON'. These traits in combination distinguish 'FIRE DRAGON' from all other commercial varieties of *Epimedium* known to the inventor. 'FIRE DRAGON' has not been tested under all possible conditions and phenotypic differences may be observed with variations in environmental, climatic and cultural conditions, without however, any variance in genotype.

1. 'FIRE DRAGON' exhibits clumping habit.
2. The foliage of 'FIRE DRAGON' is semi-evergreen.
3. 'FIRE DRAGON' exhibits large red and yellow, spurred flowers that are held above two distinct layers of foliage.
4. 'FIRE DRAGON' exhibits leaflets which are grey-brown and soft in texture when juvenile, and green and leathery in texture when mature.
5. 'FIRE DRAGON' is propagated by the method of division.
6. At maturity 'FIRE DRAGON' ranges from 45 cm. to 75 cm. in width, and ranges from 15 cm. to 25 cm. in height when in bloom.
7. Cultural requirements of 'FIRE DRAGON' are full deep shade to partial shade, fertile humus-rich soil, and regular water.
8. 'FIRE DRAGON' is hardy to minus 10° Centigrade and will retain leaves above this temperature.
9. 'FIRE DRAGON' is suitable for use in container, rock garden, or as a groundcover for the landscape.

10. 'FIRE DRAGON' blooms in March, April, May and June.

BRIEF DESCRIPTION OF THE DRAWINGS

The accompanying color drawings

Figure 1:
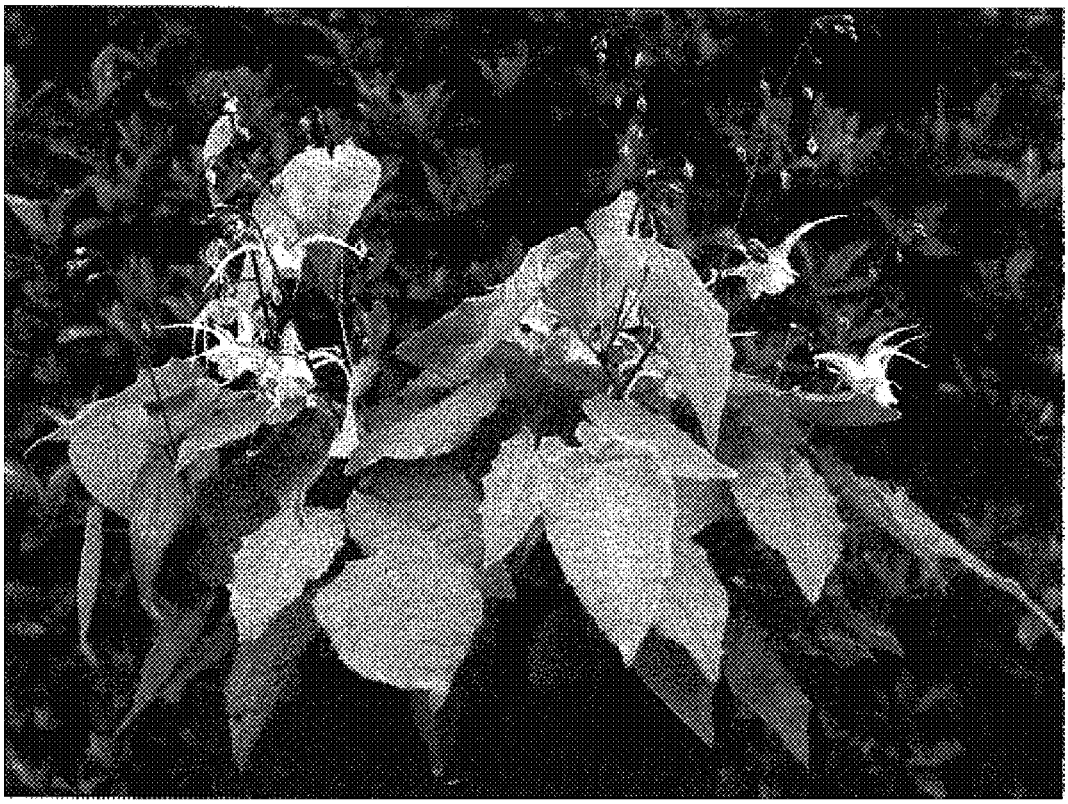
FIG. 1, FIG. 2 and FIG. 3 illustrate the overall appearance of 'FIRE DRAGON' showing the colors as true as it is reasonably possible to obtain in colored reproductions of this type. The drawings were made in May 2005 from 12-month-old plants in 2-liter containers. The plants were greenhouse grown in Hampshire, England. Colors in the drawings may differ from the color values cited in the detailed botanical description, which accurately describe the actual colors of 'FIRE DRAGON'.

The drawing labeled as FIG. 1 depicts a single whole plant of 'FIRE DRAGON' in flower.

Figure 2:
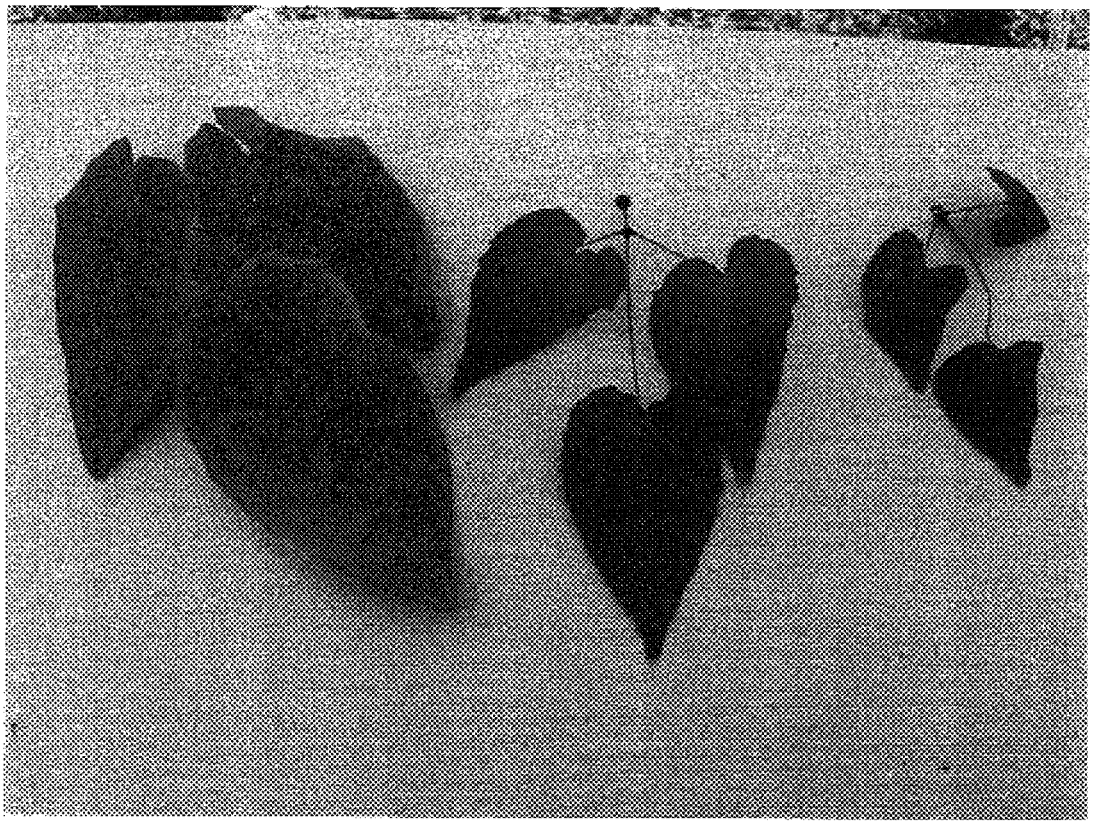

The drawing labeled as FIG. 2 depicts a close-up view of the mature and juvenile leaflets. The juvenile leaflets, shown on the right of the drawing, are initially soft and smooth and evenly tan colored. The tan coloration disappears as spring advances. The leaflets, when mature, are shown on the left of the drawing, and are leathery and uniformly green in color.

Figure 3:
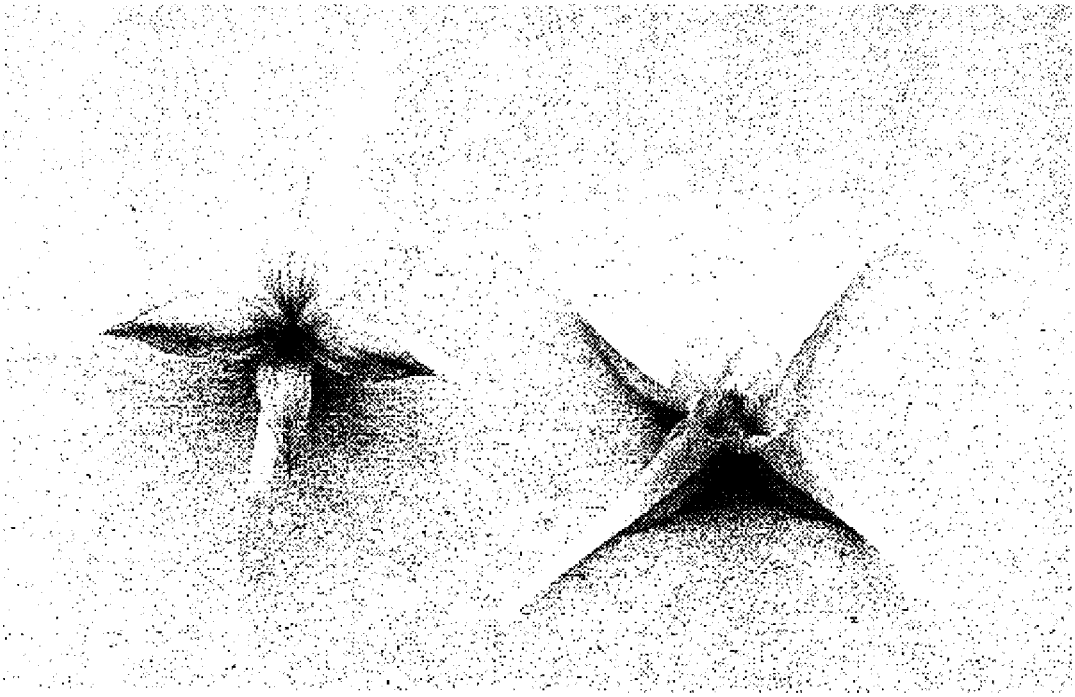

The drawing labeled as FIG. 3 depicts a close-up view of an inflorescence of 'FIRE DRAGON' which is suspended from the peduncle. The ventral aspect of the flower is downward facing and is shown on the right of the drawing with the flower rotated through 180 degrees. The dorsal aspect of the flower is shown on the left of the drawing.

FIG. 1, FIG. 2 and FIG. 3 were made using conventional techniques and although colors may appear different from actual colors due to light reflectance they are as accurate as possible by conventional photography.

BOTANICAL DESCRIPTION OF THE PLANT

The following is a detailed description of the new *Epimedium* variety named 'FIRE DRAGON'. Data was collected from 2-liter container plants that were greenhouse grown in Hampshire, England. The color determinations are in accordance with the 2001 edition of The Royal Horticultural Society Colour Chart, except where general color terms of ordinary dictionary significance are used. The growing requirements are similar to the species.

Botanical classification: *Epimedium davidii*×*E. leptorrhizum* 'FIRE DRAGON'.
Genus: *Epimedium.*
Species: *davidii*×*leptorrhizum.*
Denomination: 'FIRE DRAGON.'
Common name: Bishop's hat.
Commercial classification: Ornamental.
Plant type: Herbaceous perennial.
Commercial container size: Recommended commercial size is a 2-liter container.
Cultural requirements: Provide full deep shade to partial shade, fertile humus-rich soil, and adequate but not excess water.
Plant parentage: 'FIRE DRAGON' is a plant hybrid that resulted from the deliberate cross-hybridization of the following parent plants:
*Seed parent.*—An individual *Epimedium davidii.*
*Pollen parent.*—An individual *Epimedium leptorrhizum.*
Plant description:
*Blooming period.*—March, April, May and June.
*Plant habit.*—Clumping habit.
*Plant use.*—Grown for use in container, rock garden or as a groundcover for the landscape.
*Vigor.*—Vigorous.
*Root system.*—Fine and fibrous roots.
*Plant width* (*at maturity*).—At maturity 'FIRE DRAGON' ranges from 45 cm. to 75 cm. in width.
*Plant height* (*at maturity*).—In bloom at maturity 'FIRE DRAGON' ranges from 15 cm. to 25 cm. in height.
*Plant growth rate.*—Plant spreads by rhizomes 10 cm. to 20 cm. annually.
*Plant hardiness.*—Hardy to minus 10° Centigrade.
*Plant propagation.*—Propagation is accomplished using the method of division.
*Crop time.*—12 months are needed to produce a commercial 2-liter container plant from division.
*Special growing considerations.*—Cut back in late winter before new growth resumes, and divide clumps in spring.
*Pest or disease resistance and susceptibility.*—No particular susceptibility or resistance to pests or diseases have been noted to date. In general, *Epimediums* are considered resistant to eating or browsing by deer but such has not yet been determined or confirmed for 'FIRE DRAGON'.
Stem:
*Branching habit.*—Basal stems arise from rhizomes with some branching at or around aerial emergence. All stems appear to arise from the base. The basally branching stems bear foliage at a height of 5 cm above the foliage of the basal (rhizomatous) stems.
*Juvenile stem color.*—199A.
*Mature stem color.*—165B.
*Stem dimensions.*—Range from 1 mm. to 3 mm. in diameter and from 2 cm. to 15 cm. in height.
*Stem surface.*—Glaucous.
*Stem shape.*—Cylindrical.
*Stem texture.*—Wiry.
*Stem strength.*—Moderate.
*Stem pubescence.*—None present.
*Rhizome color.*—Colors 185A, 185B, and 186D are individually present on an individual rhizome.
*Rhizome diameter.*—Diameter ranges from 2 mm. to 2.5 mm. in diameter.
*Rhizome internode.*—Internodes range from 8 cm. to 15 cm. in length.
Foliage:
*Foliage type.*—Semi-evergreen.
*Leaf arrangement.*—Whorled.
*Leaf division.*—Biternate compound leaf.
*Basal and cauline leaflet texture* (*juvenile leaflets*).—Satiny texture.
*Basal and cauline leaflet texture* (*mature leaflets*).—Leather-like texture.
*Durability of basal and cauline leaf to stress.*—Moderate to high durability.
*Basal and cauline leaflet margins* (*juvenile and mature*). —Dentate, spiny.
*Spines.*—Spaced 4 mm to 10 mm apart, approximately 10 to 12 spines per leaflet.
*Spine length.*—0.5 mm to 1.0 mm; color: as leaf, becoming translucent at apex.
*Basal and cauline leaflet shape* (*juvenile and mature*). —Lanceolate in shape.
*Basal and cauline leaflet apex* (*juvenile and mature*). —Acuminate apex.

*Basal and cauline leaflet base* (*juvenile and mature*).—Cordate base.

*Basal and cauline juvenile leaflet pubescence* (*abaxial and adaxial surfaces*).—None observed.

*Basal and cauline mature leaflet pubescence* (*abaxial and adaxial surfaces*).—None observed.

*Basal and cauline juvenile leaflet surface* (*abaxial surface*).—Glossy surface.

*Basal and cauline juvenile leaflet surface* (*adaxial surface*).—Matte surface.

*Basal and cauline mature leaflet surface* (*abaxial surface*).—Glossy surface.

*Basal and cauline mature leaflet surface* (*adaxial surface*).—Matte surface.

*Basal and cauline juvenile leaflet length.*—Juvenile leaflet ranges from 3 cm. to 3.5 cm. in length.

*Basal and cauline mature leaflet length.*—Mature leaflet ranges from 6 cm. to 10 cm. in length.

*Basal and cauline juvenile leaflet width.*—Juvenile leaflet ranges from 1.75 cm. to 2 cm. in width.

*Basal and cauline mature leaflet width.*—Mature leaflet ranges from 3.5 cm. to 5 cm. in width.

*Basal and cauline leaflet and leaf attachment.*—Petiolate attachment.

*Basal and cauline petiole color.*—A combination of colors 199A and 165B on an individual petiole.

*Basal petiole dimensions.*—2 mm. in diameter and 5 cm. in length.

*Cauline petiole dimensions.*—2 mm. in diameter and 5 cm. in length.

*Basal and cauline petiolule color* (*juvenile and mature leaves*).—A combination of colors 199A and 165B on an individual petiolule.

*Basal petiolule dimensions* (*juvenile and mature*).—Petiolule is 1.50 mm. in diameter and ranges from 1.20 cm. to 4 cm. in length.

*Cauline petiolule dimensions* (*juvenile and mature*).—Petiolule is 1.50 mm. in diameter and ranges from 1.2 cm. to 4 cm. in length.

*Basal and cauline juvenile leaflet color* (*abaxial surface*).—Individual colors 166B, 144A, 146A and 152B are present on the juvenile leaflets of an individual plant.

*Basal and cauline juvenile leaflet color* (*adaxial surface*).—Individual colors 166B, 144A, 146A, and 152B are present on the juvenile leaflets of an individual plant.

*Basal and cauline mature leaflet color* (*abaxial surface*).—138A.

*Basal and cauline mature leaflet color* (*adaxial surface*).—138C.

*Basal and cauline venation pattern* (*juvenile and mature leaflets*).—Palmate.

*Basal and cauline juvenile leaflet vein color* (*abaxial surface*).—146A.

*Basal and cauline juvenile leaflet vein color* (*adaxial surface*).—146A.

*Basal and cauline mature leaflet vein color* (*abaxial surface*).—146A.

*Basal and cauline mature leaflet vein color* (*adaxial surface*).—138A.

*Fragrance.*—None observed.

Flower:

*Inflorescence type.*—Compound panicle.

*Number of flowers and buds.*—Flowers and buds combined range from 15 to 35 per individual 2-liter container plant.

*Bloom period.*—March, April, May and June.

*Flower shape.*—Like a bishop's hat in shape.

*Flower diameter* (*spur tip to spur tip*).—Flowers range from 3.5 cm. to 4 cm. in diameter.

*Flower depth.*—Individual flowers are 1.75 cm. in depth.

*Flower color.*—Individual colors 48B, 53D, 5C, and 2D are present on an individual flower.

*Flower petals.*—Four petals in number.

*Petals fused or unfused.*—Petals are fused.

*Petal color* (*dorsal and ventral surfaces*).—5C.

*Petal dimensions* (*length*).—17 mm to 20 mm.

*Petal dimensions* (*width, depth, at base*).—Width 6 mm, depth 5 mm.

*Petal dimensions* (*width, depth, at 5 mm from base*).—Width 1.5 mm, depth 1.5 mm.

*Calcar* (*spur*).—Four in number.

*Calcar color.*—2D.

*Calcar dimensions.*—2 mm. in diameter and 1 cm. in length.

*Bud shape.*—Globular in shape.

*Bud surface.*—Pubescent.

*Bud apex.*—Obtuse apex.

*Bud color.*—199A.

*Bud dimensions.*—4 mm. in diameter and 4 mm. in height.

*Sepals.*—8 sepals in number per individual flower, 4 dorsal sepals and 4 ventral sepals. The 4 dorsal sepals are shed as an individual flower opens.

*Dorsal sepal surface* (*abaxial surface*).—Pubescent.

*Dorsal sepal surface* (*adaxial surface*).—Pubescent.

*Ventral sepal surface* (*abaxial surface*).—Pubescent.

*Ventral sepal surface* (*adaxial surface*).—Pubescent.

*Dorsal sepal shape.*—Narrowly lanceolate in shape.

*Ventral sepal shape.*—Narrowly lanceolate in shape.

*Dorsal sepal color.*—199A.

*Ventral sepal color.*—A combination of 53D and 48B.

*Sepal margin* (*dorsal and ventral sepals*).—Entire.

*Sepal apex* (*dorsal sepal*).—Acuminate apex.

*Sepal apex* (*ventral sepal*).—Acuminate apex.

*Dorsal sepal length.*—Dorsal sepal ranges from 3 mm. to 4 mm. in length.

*Dorsal sepal width.*—Dorsal sepal ranges from 1 mm. to 1.5 mm. in width.

*Ventral sepal length.*—Ventral sepal ranges from 1 cm. to 1.2 cm. in length.

*Ventral sepal width.*—Ventral sepal ranges from 2 mm. to 3 mm. in width.

*Peduncle dimensions.*—Individual peduncle is 2 mm. in diameter and 10 cm. in length.

*Peduncle color.*—197B.

*Pedicel dimensions.*—Individual pedicel is 1.25 mm. in diameter and ranges from 1.4 cm. to 2 cm. in length.

*Pedicel color.*—197B.

*Flower fragrance.*—None observed.

Reproductive organs:

*Stamens.*—4 stamens in number.

*Stamen color.*—2A.

*Pistil.*—One pistil in number.

*Pistil color.*—2A.

*Anther color.*—2A.

*Pollen color.*—2A.

Fruit:

*Fruit shape.*—Capsular in shape.

*Fruit length.*—Fruit ranges from 1.8 cm. to 2 cm. in length.

*Fruit width.*—Fruit ranges from 1.5 mm. to 2 mm. in width.

*Fruit color.*—146B.

It is claimed:

1. A new and distinct cultivar of *Epimedium* plant named 'FIRE DRAGON', as described and illustrated herein.

* * * * *